(12) United States Patent
Henry et al.

(10) Patent No.: US 7,468,070 B2
(45) Date of Patent: Dec. 23, 2008

(54) STENT DELIVERY CATHETER

(75) Inventors: William S. Henry, San Francisco, CA (US); John E. Ortiz, East Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 799 days.

(21) Appl. No.: 10/764,054

(22) Filed: Jan. 23, 2004

(65) Prior Publication Data

US 2005/0165352 A1    Jul. 28, 2005

(51) Int. Cl.
*A61F 2/06* (2006.01)
(52) U.S. Cl. .................................................... 623/1.12
(58) Field of Classification Search ................ 623/1.11, 623/1.12, 1.23; 606/191–198
See application file for complete search history.

(56) References Cited

U.S. PATENT DOCUMENTS

| | | |
|---|---|---|
| 4,547,194 A | 10/1985 | Moorehead |
| 4,572,186 A | 2/1986 | Gould et al. |
| 4,655,771 A | 4/1987 | Wallsten |
| 4,732,152 A | 3/1988 | Wallsten et al. |
| 4,848,343 A | 7/1989 | Wallsten et al. |
| 4,990,151 A | 2/1991 | Wallsten |
| 5,026,377 A | 6/1991 | Burton et al. |
| 5,129,887 A | 7/1992 | Euteneuer et al. |
| 5,201,757 A | 4/1993 | Heyn et al. |
| 5,290,248 A | 3/1994 | Bierman et al. |
| 5,324,269 A | 6/1994 | Miraki |
| 5,360,401 A | 11/1994 | Turnland |
| 5,389,087 A | 2/1995 | Miraki |
| 5,391,172 A | 2/1995 | Williams et al. |
| 5,409,495 A | 4/1995 | Osborn |
| 5,453,090 A * | 9/1995 | Martinez et al. ............ 606/108 |
| 5,458,605 A | 10/1995 | Klemm |
| 5,458,615 A | 10/1995 | Klemm et al. |
| 5,484,444 A | 1/1996 | Braunschweiler et al. |
| 5,507,768 A | 4/1996 | Lau et al. |
| 5,533,968 A | 7/1996 | Muni et al. |
| 5,534,007 A | 7/1996 | St. Germain et al. |
| 5,558,101 A | 9/1996 | Brooks et al. |
| 5,571,168 A | 11/1996 | Toro |
| 5,579,780 A | 12/1996 | Zadini et al. |

(Continued)

FOREIGN PATENT DOCUMENTS

EP    0 303 487 A2    2/1989

(Continued)

OTHER PUBLICATIONS

U.S. Appl. No. 10/764,516 to McFerran, filed Dec. 23, 2003.

*Primary Examiner*—Kevin T Truong
(74) *Attorney, Agent, or Firm*—Crompton, Seager & Tufte, LLC

(57) ABSTRACT

A self-expanding stent delivery assembly includes a shaft having a proximal end, a distal end, a distal region, a lumen, and a longitudinal axis. A retractable sheath having an outer surface, a proximal end and a distal end is co-axially disposed around the shaft distal region. A stent is disposed co-axially between the shaft and the retractable sheath. A tubular tapered tip is affixed to the retractable sheath distal end. The tubular tapered tip has an elongate region predisposed to fracturing. Methods of delivering a self-expanding stent are also described.

19 Claims, 3 Drawing Sheets

U.S. PATENT DOCUMENTS

| | | | |
|---|---|---|---|
| 5,591,172 A | 1/1997 | Bachmann et al. | |
| 5,593,412 A | 1/1997 | Martinez et al. | |
| 5,690,644 A | 11/1997 | Yurek et al. | |
| 5,690,645 A | 11/1997 | Van Erp | |
| 5,709,703 A | 1/1998 | Lukic et al. | |
| 5,743,874 A | 4/1998 | Fischell et al. | |
| 5,772,669 A | 6/1998 | Vrba | |
| 5,776,142 A | 7/1998 | Gunderson | |
| 5,782,855 A | 7/1998 | Lau et al. | |
| 5,807,327 A | 9/1998 | Green et al. | |
| 5,843,028 A | 12/1998 | Weaver et al. | |
| 5,921,968 A | 7/1999 | Lampropoulos et al. | |
| 5,921,971 A | 7/1999 | Agro et al. | |
| 5,957,974 A * | 9/1999 | Thompson et al. | 623/1.13 |
| 5,980,532 A | 11/1999 | Wang | |
| 5,980,533 A | 11/1999 | Holman | |
| 5,989,280 A | 11/1999 | Euteneuer et al. | |
| 6,007,522 A | 12/1999 | Agro et al. | |
| 6,007,543 A | 12/1999 | Ellis et al. | |
| 6,059,752 A | 5/2000 | Segal | |
| 6,074,398 A | 6/2000 | Leschinsky | |
| 6,077,295 A | 6/2000 | Limon et al. | |
| 6,113,607 A | 9/2000 | Lau et al. | |
| 6,117,140 A | 9/2000 | Munsinger | |
| 6,120,522 A | 9/2000 | Vrba et al. | |
| 6,228,110 B1 | 5/2001 | Munsinger | |
| 6,235,051 B1 | 5/2001 | Murphy | |
| 6,287,329 B1 | 9/2001 | Duerig et al. | |
| 6,302,893 B1 | 10/2001 | Limon et al. | |
| 6,322,586 B1 | 11/2001 | Monroe et al. | |
| 6,342,066 B1 | 1/2002 | Toro et al. | |
| 6,383,344 B1 | 5/2002 | Miller et al. | |
| 6,391,051 B2 | 5/2002 | Sullivan, III et al. | |
| 6,398,802 B1 | 6/2002 | Yee | |
| 6,425,898 B1 | 7/2002 | Wilson et al. | |
| 6,428,566 B1 | 8/2002 | Holt | |
| 6,471,718 B1 | 10/2002 | Staehle et al. | |
| 6,478,814 B2 | 11/2002 | Wang et al. | |
| 6,494,889 B1 | 12/2002 | Fleischman et al. | |
| 6,514,261 B1 | 2/2003 | Randall et al. | |
| 6,517,548 B2 | 2/2003 | Lorentzen Cornelius et al. | |
| 6,530,947 B1 | 3/2003 | Euteneuer et al. | |
| 6,554,848 B2 | 4/2003 | Boylan et al. | |
| 6,576,006 B2 | 6/2003 | Limon et al. | |
| 6,582,460 B1 | 6/2003 | Cryer | |
| 6,592,549 B2 | 7/2003 | Gerdts et al. | |
| 6,607,551 B1 | 8/2003 | Sullivan et al. | |
| 6,613,075 B1 | 9/2003 | Healy et al. | |
| 6,623,491 B2 | 9/2003 | Thompson | |
| 6,623,518 B2 | 9/2003 | Thompson et al. | |
| 6,656,212 B2 | 12/2003 | Ravenscroft et al. | |
| 6,656,213 B2 | 12/2003 | Solem | |
| 6,663,660 B2 | 12/2003 | Dusbabek et al. | |
| 6,723,071 B2 | 4/2004 | Gerdts et al. | |
| 6,899,727 B2 * | 5/2005 | Armstrong et al. | 623/1.12 |
| 2001/0044648 A1 | 11/2001 | Wolinsky et al. | |
| 2002/0111666 A1 | 8/2002 | Hart et al. | |
| 2002/0193863 A1 | 12/2002 | Rourke et al. | |
| 2003/0153941 A1 | 8/2003 | Rourke | |

FOREIGN PATENT DOCUMENTS

| | | |
|---|---|---|
| EP | 0 505 686 A1 | 9/1992 |
| EP | 0 627 201 B1 | 12/1994 |
| EP | 0 696 447 A2 | 2/1996 |
| EP | 0 873 733 A1 | 10/1998 |
| WO | WO 98/11846 | 3/1998 |
| WO | WO 99/49808 A1 | 10/1999 |
| WO | WO 00/67675 | 11/2000 |
| WO | WO 00/69498 A1 | 11/2000 |
| WO | WO 01/34061 A1 | 5/2001 |

* cited by examiner

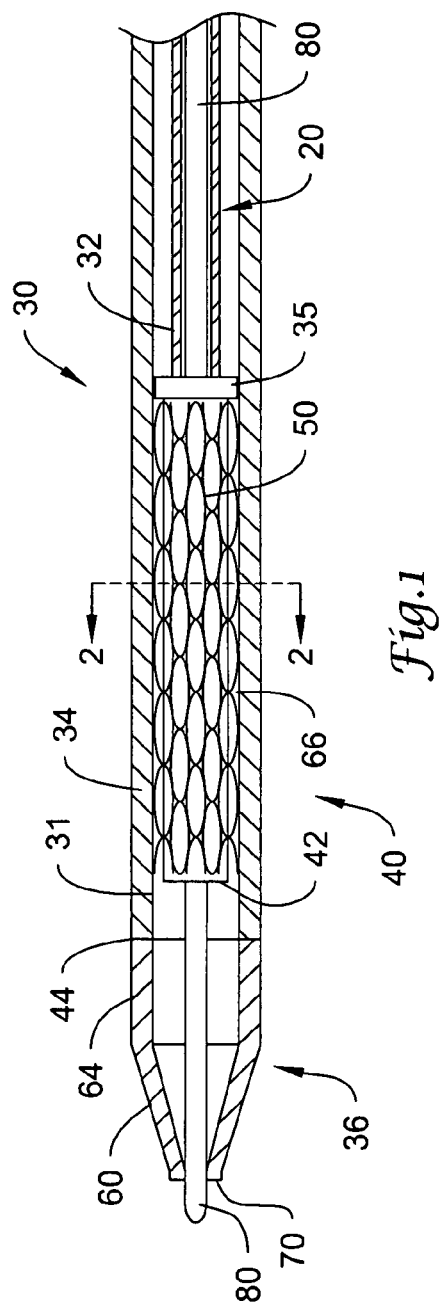
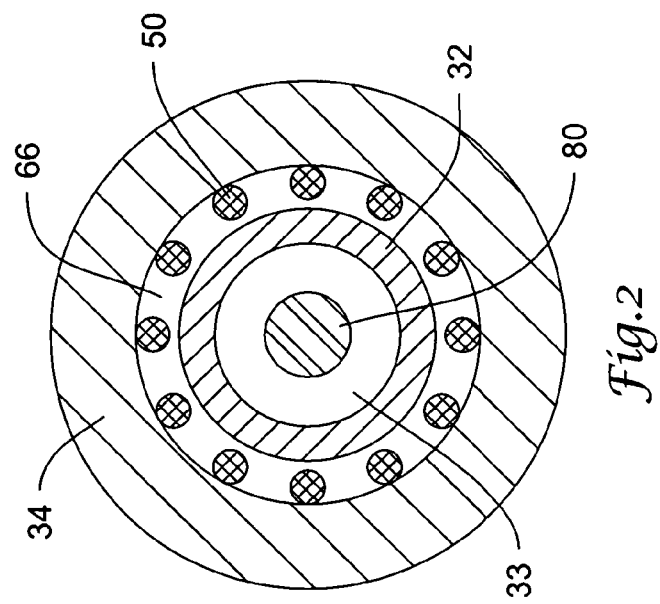

ically, the present invention is related to catheters. The present invention includes stent delivery catheter apparatus with a tapered tip that is fracturable during deployment of a self-expanding stent that has been loaded onto the catheter.

STENT DELIVERY CATHETER

FIELD OF THE INVENTION

The present invention is related generally to medical devices. More specifically, the present invention is related to catheters. The present invention includes stent delivery catheter apparatus with a tapered tip that is fracturable during deployment of a self-expanding stent that has been loaded onto the catheter.

BACKGROUND OF THE INVENTION

Atherosclerotic disease is a leading cause of death in the industrialized world, particularly in the United States. Many heart attacks and strokes are caused in part by a narrowed, stenosed blood vessel. A medical procedure commonly used to deal with vessel stenosis is angioplasty. Angioplasty, in particular Percutaneous Transluminal Angioplasty (PTA), includes inserting a balloon catheter into the femoral artery near the groin, and advancing the catheter to the stenosis. The balloon can then be inflated to widen or dilate the narrowed region. The balloon catheter can then be withdrawn. In some cases, the widened vessel rebounds or re-closes, narrowing the vessel over a period of time.

Stents have come into increasing use to prevent the widened vessel regions from narrowing after angioplasty. A stent, typically having a tubular shape, can be put in place in the widened vessel region to hold the vessel walls apart and the lumen open in the event the conditions would otherwise result in re-stenosis. One class of stents requires that the stent be forcibly outwardly expanded to put the stent into position against the vessel walls. Another class of stents, self-expanding stents, can be delivered to a site in a compressed or constrained configuration and released in the vessel region to be supported. The self-expanding stent then expands in place to a configuration having a wide lumen, typically pressing firmly against the vessel walls where released. The stent is commonly placed at a recently dilated, stenosed vessel region.

Self-expanding stents can be delivered to a target site mounted over an inner tube or shaft and constrained within the distal end of an enclosing retractable tube or sleeve. The self-expanding stent can be freed from the restraint of the outer sheath by either distally pushing the inner shaft against the stent or proximally pulling the retractable outer sheath from over the stent. Once free of the outer restraint, the self-expanding stent can expand to force itself against the vessel inner walls. Self-expanding stents are often elastically biased to assume an original larger shape after being temporarily compressed into a smaller size to more easily be transported through blood vessels to the target site. There is an ongoing need for improvements in catheters that deliver self-expanding stents.

SUMMARY OF THE INVENTION

Generally, the present invention relates to a stent delivery device having a tapered tip that is fracturable during deployment or by deploying a self-expanding stent from the stent delivery device.

In one embodiment, a self-expanding stent delivery assembly includes a shaft having a proximal end, a distal end, a distal region, a lumen, and a longitudinal axis. A retractable sheath having an outer surface, a proximal end and a distal end is co-axially disposed around the shaft distal region. A stent is disposed co-axially between the shaft and the retractable sheath. A tubular tapered tip is bonded to the retractable sheath distal end. The tubular tapered tip has an elongate region predisposed to fracturing.

In another embodiment, a method of delivering a self-expanding stent includes placing a stent delivery device at a target site. The stent delivery device includes a shaft having a proximal end, a distal end, a distal region, a lumen, and a longitudinal axis; a retractable sheath having a proximal end and a distal end co-axially disposed around the shaft distal region; a stent disposed co-axially between the shaft and the retractable sheath; and a tubular tapered tip bonded to the retractable sheath distal end, the tubular tapered tip having an elongate region predisposed to fracturing. The stent is deployed at the target site by retracting the retractable sheath or advancing the stent and fracturing the elongate region predisposed to fracturing. The stent delivery device is then removed from the target site.

The above summary of the present invention is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1 is a partial longitudinal cross-sectional view of a stent delivery device;

FIG. 2 is a cross-sectional view of the stent delivery device of FIG. 1 taken along line 2-2;

Figure 3:
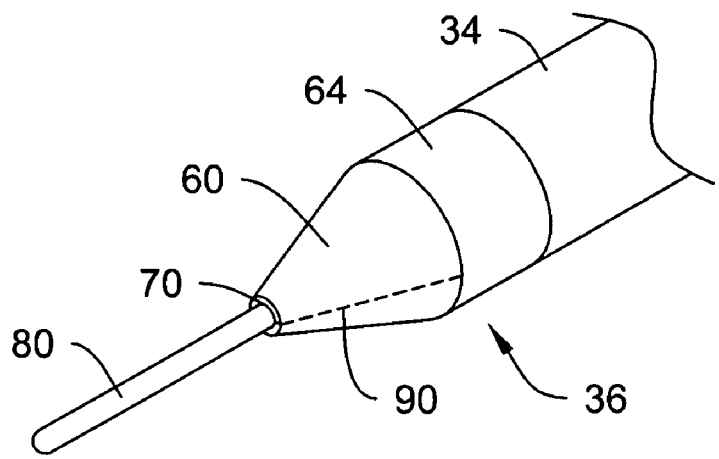
FIG. 3 is a perspective view of a tapered tip.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENTS

The stent delivery device and method for using the stent delivery device of the present invention are believed to be applicable to a variety of applications where delivery of stents is desired, for example, atherosclerotic stent delivery. While the present invention is not so limited, an appreciation of various aspects of the invention will be gained through a discussion of the examples provided below.

The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. Thus, for example, reference to "an elongate region" includes two or more elongate regions. As used in this specification and the appended claims, the term "or" is generally employed in its sense including "and/or" unless the content clearly dictates otherwise.

Also, while the tubular members illustrated in the Figures have generally circular cross sections, this is not a necessary part of the present invention, and the tubular members are merely shown as such for purposes of simplicity in illustration.

FIG. 1 illustrates a stent delivery device or catheter 30. Catheter assembly 30 includes an inner tube 32 having a lumen 33 therethrough (as shown in FIG. 2), a distal region 40 and a distal end 42. Inner tube 32 is preferably formed of a metal, polymeric material, or polymeric/metal composite material suitable for delivering a stent through tortuous vessel passages and in one embodiment, is suitable for receiving a guidewire therethrough. One useful material can include a braided polyamide tubing. In an illustrative embodiment, the catheter assembly 30 can be guided to the target site via a guidewire 80. In the illustrative embodiment, the guidewire 80 can be within the inner tube 32 lumen 33. The guide wire can be any operable diameter such as, for example, 0.01 to 0.04 inch or 0.014 to 0.035 inch, however a guide wire is not required in all embodiments.

In an illustrative embodiment, a retractable sheath 34 having a distal region or end 44 is slidably disposed over inner tube 32, having an annular space 66 sufficient in size to receive a compressed stent between inner tube 32 and retractable sheath 34. Alternatively or in addition, the retractable sheath 34 can remain static, and a stent or inner tube 32 can be advancable relative to the retractable sheath 34. Retractable sheath 34 can be formed of a metal, polymeric material, or polymeric/metal composite material preferably sufficiently lubricious to ease in advancing catheter assembly 30 through increasingly smaller blood vessels. Sheath 34 can be formed from a variety of materials such as, for example, high density polyethylene, nylon, reinforced nylons, or polyurethanes. Sheath 34 can have an inner layer 31 including a lubricious material such as, for example, polytetrafluoroethylene.

In an illustrative embodiment, a stop 35 is affixed to the inner tube 32 proximal of its distal end 42, about the length of a stent 50 and near the distal end of the catheter 30. The stop 35 functions to hold the stent 50 axially during deployment of the stent 50 relative to the outer tube 34.

A distally positioned tapered tip 36 is disposed distal to or adjacent to the inner tube distal region 40 and is affixed to or formed integral with retractable sheath 34. In one embodiment, tapered tip 36 can be formed of a shrinkable film material, for example, a heat-shrinkable material such as polyolefin copolymer, nylon, or polytetrafluoroethylene. In another embodiment, tapered tip 36 can be formed of the same or similar material to the material forming the retractable sheath 34. In another embodiment, the tapered tip 36 can be formed from the same layer of material forming at least a portion of the retractable sheath 34. If necessary, the tapered tip 36 can be secured to retractable sheath 34 using a variety of methods such as, for example, molding, extrusion, heat bonding, adhesives, laser bonding, or solvent welding, using methods well known to those skilled in the art. Any type of connection means may be used to affix the tapered tip 36 to the retractable sheath 34. This connection means can include, for example, a lap joint, butt joint or integral molding. Alternatively or in addition, a mechanical connection such as threads or friction fit could be utilized. In an illustrative embodiment, the tapered tip 36 can include a waist portion 64 and a free portion 60. In the illustrative embodiment shown, the tapered tip 36 is formed integrally with retractable sheath 34 and the outer surface of the tapered tip 36 is continuous with the outer surface of the retractable sleeve 34, thus the connection is smooth and substantially free of transitions.

Tapered tip 36 is illustrated having an open distal end 70. However, the tapered tip 36 can have a closed distal end 70. The open distal end 70 can be sized and configured to slidably engage or pass the guide wire 80. However, a guide wire 80 is not required in all embodiments. In the illustrative embodiment, the waist portion 64 can be disposed to and affixed to the distal end 44 of the retractable sheath 34. The free portion 60 can extend distally beyond the distal end 44 of the retractable sheath 34.

The tapered tip 36 can aid in tracking stent delivery device 30 through vessel passages and turns. In an illustrative embodiment, the tapered tip 36 is conically tapered. However, the tapered tip 36 can have an arcuate taper or any arrangement of constant diameters and tapers, as desired.

As depicted in FIG. 3, the tubular tip 36 has at least one elongate region predisposed to fracturing 90. The tubular tip 36 can have 2, 3, 4, 5, 6, 7, 8, 9, 10 or more elongate regions predisposed to fracturing 90. The elongate region predisposed to fracturing 90 fractures the tapered tip to expand the open distal end 70 and allows the stent 50 to pass through the fractured tapered tip 36 open distal end 70 generally unimpeded. In an illustrative embodiment, the elongate region predisposed to fracturing 90 can be co-planar with a longitudinal axis running along the length of the stent delivery device 30. The elongate region predisposed to fracturing 90 can be formed on the tapered tip 36 before the tapered tip 36 is affixed to the retractable sheath 34, or formed during the process of affixing the tapered tip 36 to the retractable sheath 34 or integrally forming the tapered tip 36 from the layer of material forming at least a portion of the retractable sheath 34, or after affixing/integrally forming the tapered tip 36 with the retractable sheath 34.

In an illustrative embodiment, the elongate region predisposed to fracturing 90 can be a line of perforations that extend through a portion of or through the entire tubular tip 36 wall thickness. The elongate region predisposed to fracturing 90 can be a score line that extends through a portion of the tubular tip 36 wall thickness where the wall thickness along the score line 90 is less than the thickness along the remaining tubular tip 36 wall. Alternatively or in addition, the elongate region predisposed to fracturing 90 can be material having a tensile strength that is less than the tensile strength of the remaining tubular tip 36.

FIG. 2 is a cross-sectional view of the stent delivery device of FIG. 1 taken along line 2-2. An inner lumen 33 is coaxially disposed about a guidewire 80. A self-expanding stent 50 can be placed into annular space 66 between retractable sheath 34 and inner tube 32.

In an illustrative embodiment, the stent 50 can be placed over the inner tube 32 by sliding the stent 50 proximally over the inner tube distal end 42. Stent 50 can be compressed using a suitable tool or jig, to decrease the outer diameter of the stent 50 to a size compatible with the annular space 66. With the stent 50 compressed, the stent 50 can be axially and proximally slid over inner tube 32 and within sleeve distal region 44, to reside in annular space 66. With the stent 50 constrained by retractable sleeve 34, any restraining tool or jig can be removed from the catheter. With stent 50 in position, tubular tip 36 can be affixed to retractable sheath 34 distal end 44.

In another illustrative embodiment, a compressed stent 50 can be placed onto the inner tube 32 and loaded into the catheter 30 from a proximal end of the catheter 30. The inner tube 32 and compressed stent 50 can be moved toward the sleeve distal region 44. The tubular tip 36 can be attached to the retractable sheath 34 prior to loading the compressed stent 50 into the catheter 30.

In an illustrative embodiment, the retractable sheath 34 can be any material as described above such as, for example, a clear medical grade PTFE (polytetrafluoroethylene) extrusion which covers the distal 2-20 cm (depending on stent length) of the stent delivery device 30. However, the retractable sheath 34 could be made of any suitable material as described above. A specific alternative embodiment could utilize a fluoropolymer material which is transparent to visible light to enable the operator to directly view deployment in an endoscopic delivery procedure. Such materials are well known in the art. In an illustrative embodiment, self-expanding nitinol stents of from 1-15 mm or 6-14 mm in diameter and ranging from 1-100 mm or 5-50 mm in length can be accommodated. It should be understood that any type of self-expanding stent could be employed. In an illustrative embodiment, the retractable sheath 34 can be connected to a proximal retraction handle (not shown) by a stainless steel pull-wire. In this embodiment, the proximal end of retractable sheath 34 slidably seals to elongate shaft 20, permitting it to slide proximally along elongate shaft when retracted by pull-wire. In another illustrative embodiment, the stent delivery system can include a rapid exchange guide wire system.

The stent 50 can be compressed at low temperature for loading into delivery system 30 and held in its reduced delivery configuration by retractable sheath 34. Upon deployment in vivo at body temperature, the original stent shape can be restored as the nitinol stent self-expands, exerting radial force on the constricted portion of the body lumen to re-establish patency. A stent delivery catheter showing the retraction handle is described in U.S. Pat. No. 6,391,051, which is incorporated by reference herein.

FIG. 3 is a perspective view of a tapered tip 36 prior to deploying a stent 50. As described above, a tubular tip 36 can be affixed to the distal end 44 of the retractable sheath 34. In the illustrative embodiment, the tubular tip 36 includes a waist portion 64 and a tapered portion 60. The waist portion 64 is shown integrally bonded to or integrally formed with the distal region or end 44 of the retractable sheath 34 providing a continuous and/or smooth outer surface across the tubular tip 36 and retractable sheath 34. In the illustrative embodiment, the tubular tip 36 has an open distal end 70 with an inner diameter that is less than the inner diameter of the waist portion 64 and is sized and configured to engage a guidewire 80, but this is not required in all embodiments. The tubular tip 36 has at least one elongate region 90 predisposed to fracturing as described above.

Figure 4:
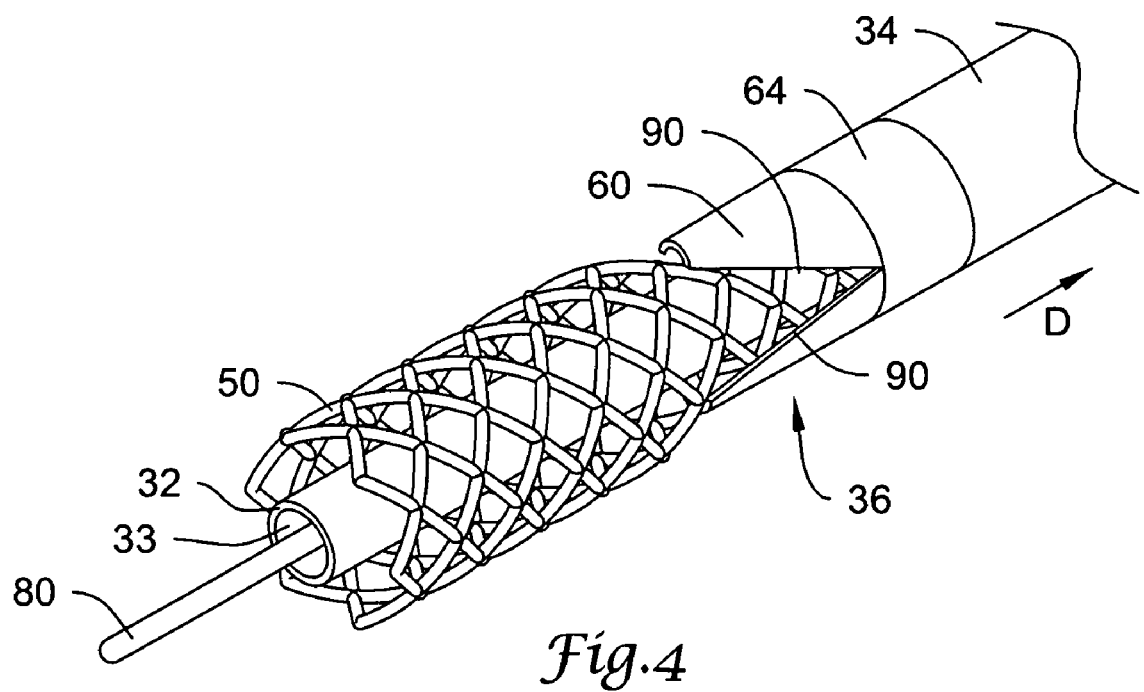
FIG. 4 is a perspective view of the tapered tip of FIG. 3 while partially deploying a stent.

FIG. 4 is a perspective view of the tapered tip of FIG. 3 while partially deploying a stent 50. As the retractable sheath 34 is moved toward the elongate shaft 20 in the direction D, the elongate region predisposed to fracturing 90 fractures and the tapered tip 36 expands to allow the stent 50 to expand away from the inner tube 32 and onto the target site. The stent 50 fractures the tapered tip 36 as the stent 50 passes through the tapered tip 36 substantially unencumbered.

Figure 5:
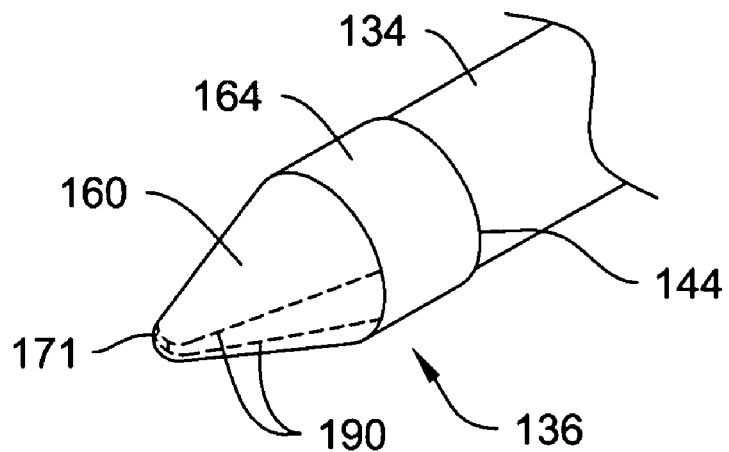
FIG. 5 is a perspective view of another embodiment of a tapered tip.

FIG. 5 is a perspective view of another tapered tip 136 prior to deploying a stent 150. As described above, a tubular tip 136 can be affixed to the distal region or end 144 of the retractable sheath 134. The tubular tip 136 includes a waist portion 164 and a tapered free portion 160. The waist portion 164 can be bonded to the distal end 144 of the retractable sheath 134. The tubular tip 136 has a closed distal end 171 with an inner diameter that is less than the inner diameter of the waist portion 164. The tubular tip 136 has at least two elongate regions 190 predisposed to fracturing as described above.

Figure 6:
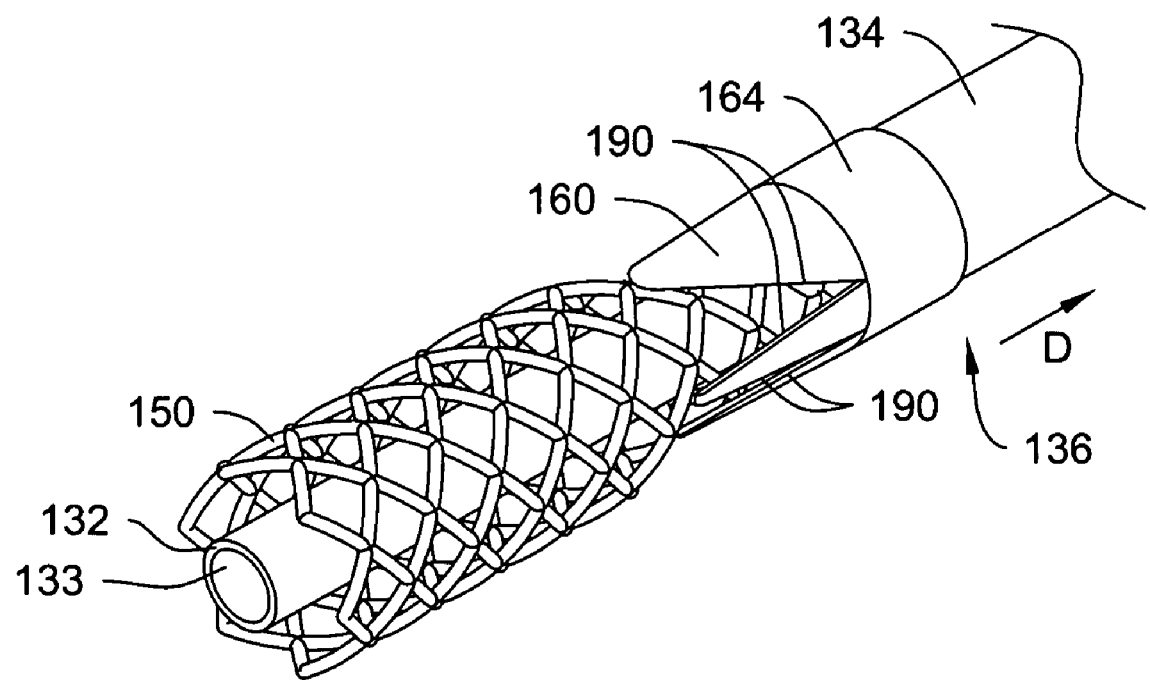
FIG. 6 is a perspective view of the tapered tip of FIG. 5 while partially deploying a stent.

FIG. 6 is a perspective view of the tapered tip of FIG. 5 while partially deploying a stent 150. As the retractable sheath 134 is moved toward the elongate shaft in the direction D, the elongate regions predisposed to fracturing 190, fractures and the tapered tip 136 expands to allow the stent 150 to expand away from the inner tube 132 and onto the target site. The stent 150 fractures the tapered tip 136 as the stent 150 passes through the tapered tip 136 substantially unencumbered.

Alternatively in some embodiments, the stent 150 may be deployed by advancing the inner tube 132 or stent 150 through the tapered tip 136 in an opposite direction to direction D. Similarly to above, the elongate regions predisposed to fracturing 190, fractures and the tapered tip 136 expands to allow the stent 150 to expand away from the inner tube 132 and onto the target site. The stent 150 fractures the tapered tip 136 as the stent 150 passes through the tapered tip 136 substantially unencumbered.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A self-expanding stent delivery assembly comprising:
   a shaft having a distal region and a longitudinal axis;
   a retractable sheath having a proximal end and a distal end, the retractable sheath co-axially disposed around at least the shaft distal region;
   a stent disposed co-axially between the shaft and the retractable sheath in the distal region;
   a stop member coupled to the shaft and positioned proximally of the stent; and
   a tubular tapered tip affixed to the retractable sheath distal end, the tubular tapered tip having an elongate region predisposed to fracturing.

2. The self-expanding stent delivery assembly according to claim 1, wherein the tubular tapered tip has a plurality of elongate regions predisposed to fracturing where each elongate region predisposed to fracturing is co-planar with the longitudinal axis.

3. The self-expanding stent delivery assembly according to claim 1, wherein the elongate region predisposed to fracturing is a line of perforations.

4. The self-expanding stent delivery assembly according to claim 1, wherein the tubular tip has a first thickness and the elongate region predisposed to fracturing has a second thickness that is less than the first thickness.

5. The self-expanding stent delivery assembly according to claim 1, wherein the tubular tip is formed of a first material having a first tensile strength and the elongate region predisposed to fracturing is formed of a second material having a second tensile strength that is less than the first tensile strength.

6. The self-expanding stent delivery assembly according to claim 1, further comprising a guidewire disposed within the shaft lumen.

7. The self-expanding stent delivery assembly according to claim 6, wherein the tubular tip has a distal end defining a tip opening, the tip opening sized and configured to surround the guidewire.

8. The self-expanding stent delivery assembly according to claim 1, wherein the tubular tip has a proximal waist portion bonded to the distal end of the retractable shaft.

9. The self-expanding stent delivery assembly according to claim 8, wherein the tubular tip waist portion is bonded to the outer surface of the retractable shaft.

10. The self-expanding stent delivery assembly according to claim 1, wherein the tubular tip is integrally bonded to or integrally formed with the retractable sheath distal end forming a continuous smooth outer surface across the tubular tip and retractable sleeve.

11. A method of delivering a self-expanding stent comprising:
   placing a stent delivery device at a target site, the stent delivery device comprising:
      a shaft having a distal region and a longitudinal axis;
      a retractable sheath having a proximal end and a distal end, the retractable sheath co-axially disposed around the shaft distal region;
      a stent disposed co-axially between the shaft and the retractable sheath in the distal region;
      a stop member coupled to the shaft and positioned proximally of the stent; and
      a tubular tapered tip affixed to the retractable sheath distal end, the tubular tapered tip having an elongate region predisposed to fracturing;
   deploying the stent at the target site by retracting the retractable sheath or advancing the stent and fracturing the elongate region predisposed to fracturing; and
   removing the stent delivery device from the target site.

12. The method according to claim 11, wherein the step of deploying the stent at the target site comprises deploying the stent at the target site by retracting the retractable sheath or advancing the stent and fracturing the elongate region predisposed to fracturing as the stent passes through the tubular tip.

13. The method according to claim 11, wherein the tubular tapered tip has a plurality of elongate regions predisposed to fracturing and the step of deploying the stent at the target site comprises retracting the retractable sheath or advancing the stent and fracturing the plurality of elongate regions predisposed to fracturing.

14. The method according to claim 13, wherein the step of deploying the stent at the target site comprises deploying the stent at the target site by retracting the retractable sheath or advancing the stent and fracturing the plurality of elongate regions predisposed to fracturing as the stent passes through the tubular tip.

15. The method according to claim 11, wherein the stent passes through the tubular tip during deployment and the tubular tip is integrally bonded to or integrally formed with the retractable sheath distal end forming a continuous smooth outer surface across the tubular tip and retractable sleeve.

16. The method according to claim 11, further comprising the step of placing a guidewire across the target site prior to placing the stent delivery device at the target site.

17. The method according to claim 16, wherein the step of placing a guidewire across the target site prior to placing the stent delivery device at the target site comprises providing a tubular tip having a distal end defining a tip opening, the tip opening sized and configured to surround the guidewire.

18. The method according to claim 17, wherein the step of placing a guidewire across the target site prior to placing the stent delivery device at the target site comprises providing a tubular tip having a distal end defining a tip opening, the tubular tip having a proximal waist portion bonded to the distal end of the retractable shaft.

19. The method according to claim 16, wherein the step of placing a guidewire across the target site prior to placing the stent delivery device at the target site further comprises using the guidewire to place the stent delivery device at the target site.

* * * * *